United States Patent [19]

Jenkins et al.

[11] 4,019,863
[45] Apr. 26, 1977

[54] SELECTIVE DETECTION OF A CONSTITUENT IN AN ATMOSPHERE

[76] Inventors: Anthony Jenkins, 54 Finchams Close, Linton, Cambridgeshire; James Ephraim Lovelock, Bowerchalke, Salisbury, Wiltshire, both of England

[22] Filed: Apr. 8, 1975

[21] Appl. No.: 566,057

[30] Foreign Application Priority Data

Apr. 8, 1974 United Kingdom ............. 15556/74

[52] U.S. Cl. ........................... 23/232 E; 23/254 E; 23/255 E; 73/421.5 R
[51] Int. Cl.² ..................... G01N 1/22; G01N 33/22
[58] Field of Search ......... 23/254 R, 254 E, 255 R, 23/255 E, 232 R, 232 E, 253 PC; 73/421.5 R

[56] References Cited
UNITED STATES PATENTS

| | | | |
|---|---|---|---|
| 3,403,978 | 10/1968 | Favre | 23/254 X |
| 3,425,807 | 2/1969 | Levy | 23/254 X |
| 3,535,084 | 10/1970 | Izawa et al. | 23/254 R |
| 3,753,653 | 8/1973 | Brieva et al. | 23/254 X |
| 3,883,739 | 5/1975 | Jenkins | 23/254 E |
| 3,892,968 | 7/1975 | Lovelock | 250/389 |

*Primary Examiner*—R.E. Serwin
*Attorney, Agent, or Firm*—Woodhams, Blanchard and Flynn

[57] ABSTRACT

A method and apparatus for selectively detecting the presence and concentration of a constituent in a gas sample, such as for example the presence of the vapors emitted by explosives and drugs in the atmosphere. A sample flow is drawn through a switching device into a detector and the output of the detector is correlated with the operation of the switching device. The switching device is actuated at periodic intervals between first and second conditions. In the first condition the switching device interrupts the flow of the constituent of interest to the detector while allowing the remainder of the sample to pass into the detector. In the second condition all the gas sample passes into the detector. The changes in detector output result from the presence of the constituent and the magnitude of the changes indicate the concentration of the constituent in the gas sample.

16 Claims, 9 Drawing Figures

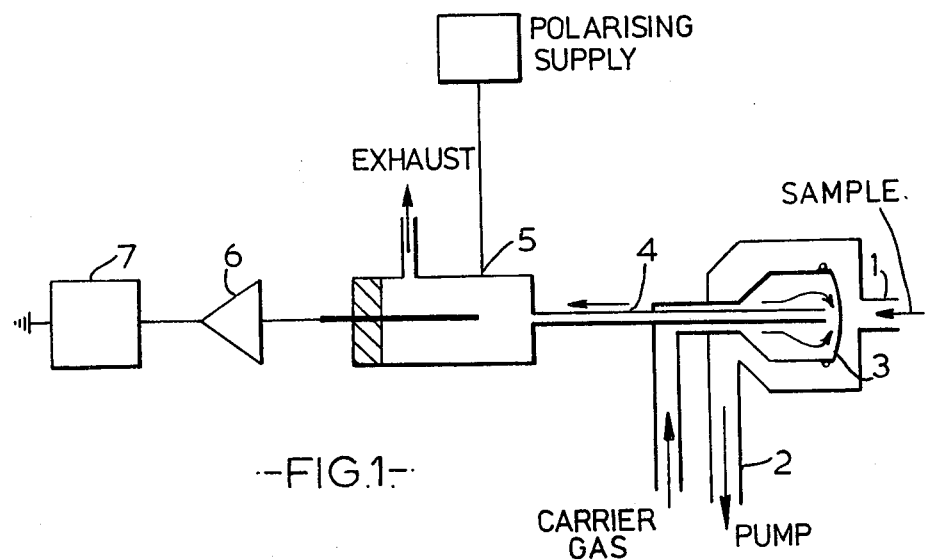
-FIG.1-
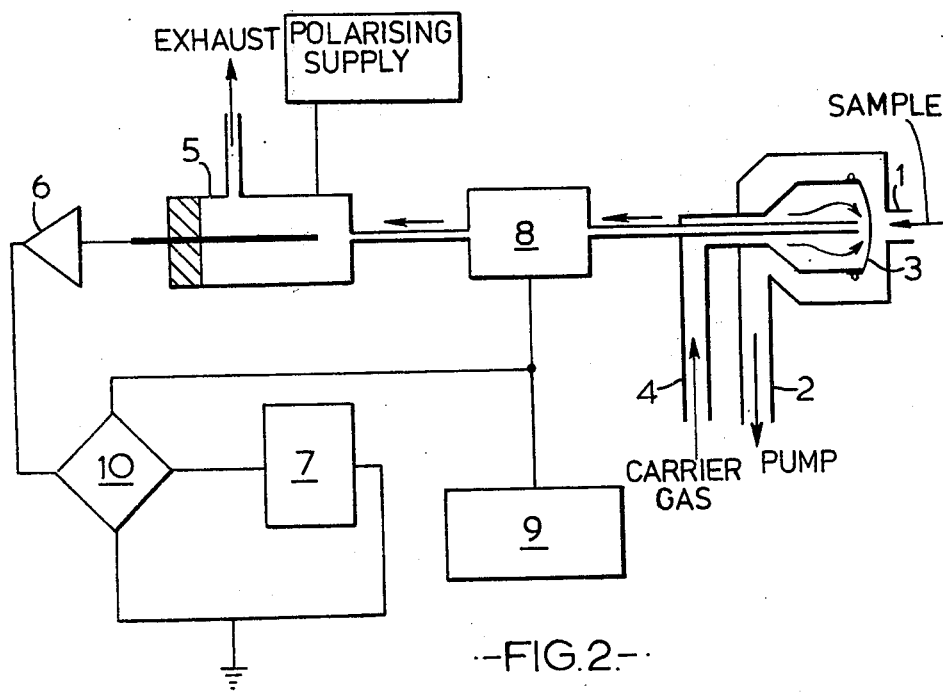
-FIG.2-

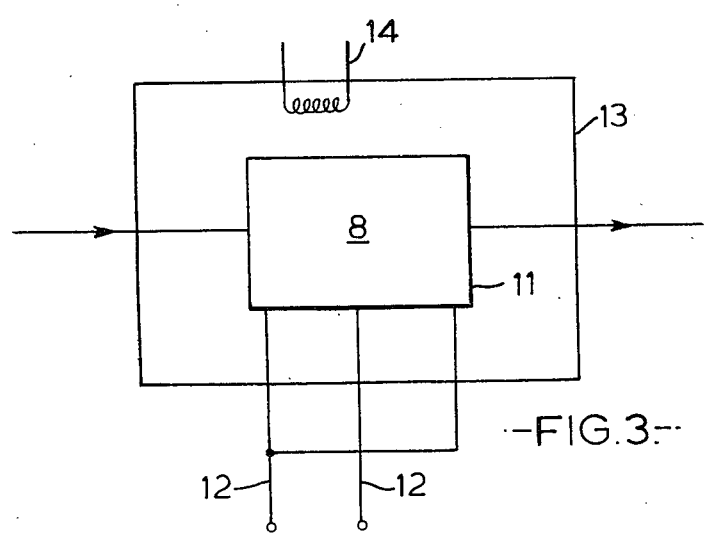
-FIG.3.-
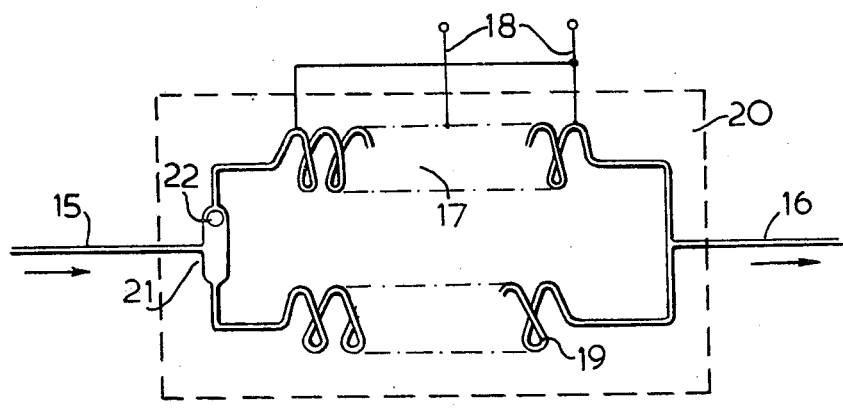
-FIG.4.-
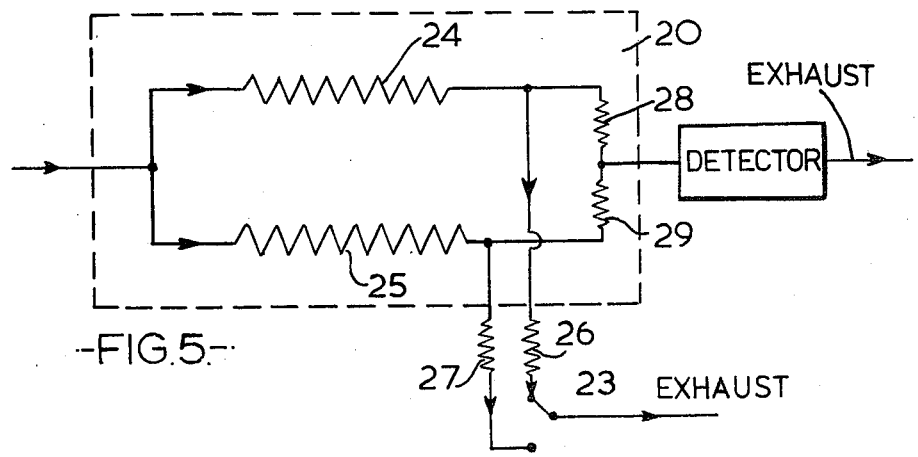
-FIG.5.-

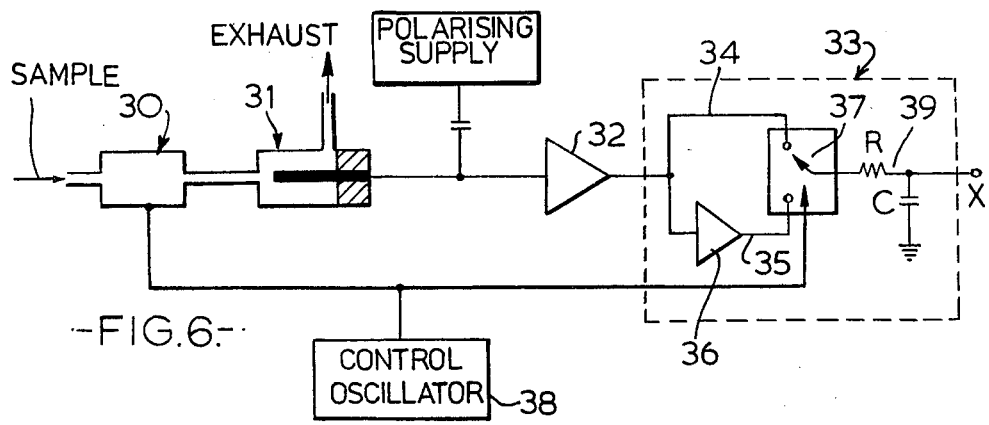
-FIG.6.-
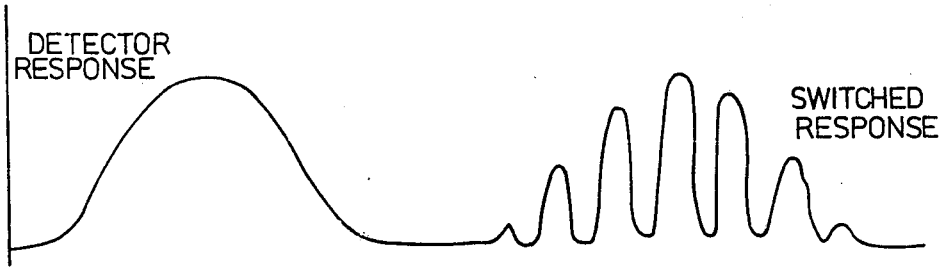
-FIG.7.-
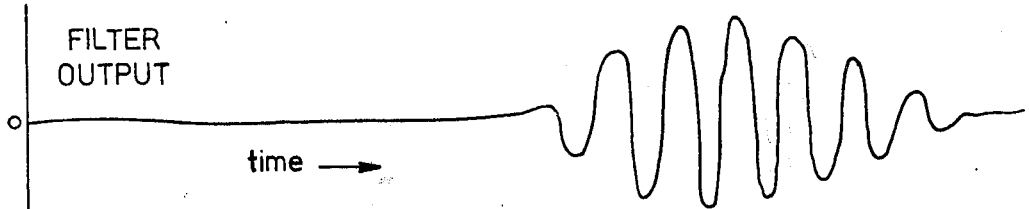
-FIG.8.-
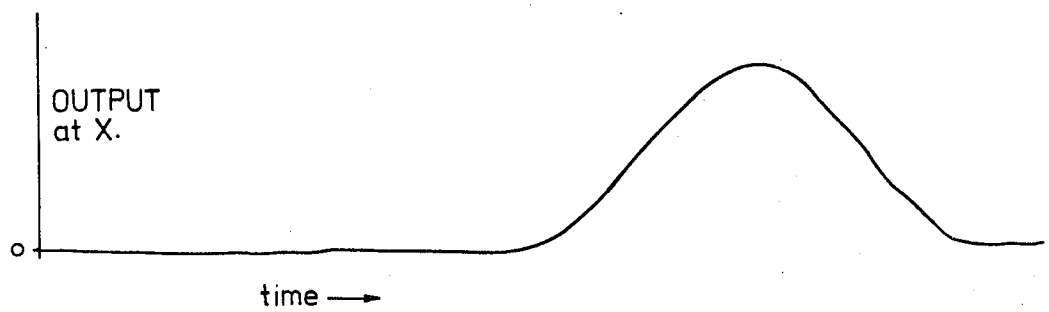
-FIG.9.-

SELECTIVE DETECTION OF A CONSTITUENT IN AN ATMOSPHERE

The present invention concerns a method and apparatus for detecting the presence of a particular component of interest in an atmosphere.

In order to detect and distinguish a component of interest in a mixture containing the component it is necessary to rely upon a property of the component which is peculiar to the component only and is not exhibited by the remaining components of the mixture. However it frequently happens that a detector employed to detect the presence of a particular component of interest is also sensitive to the presence of other components in the gas flow. Signals resulting from these other components, can, for convenience be termed background noise. In many applications this background noise can be such as to mask any signal resulting from the presence of the component of interest. The background noise can arise through concentrations of other responsive components in a gas flow entering a detector and examples of this occur in gas chromatography when employing, for example, flame ionisation detectors, argon ionisation detectors and electron capture detectors. Random background noise can also result from instrumental parameters such as variations of the emission from the radioactive source in the argon ionisation and electron capture detectors.

The present invention seeks to avoid the above disadvantages and to make it possible whereby a component of interest can be positively detected and distinguished in a detector even when the component is admixed in a gas flow with other components capable of giving a response in the detector.

Basically, the invention comprises periodically interrupting the flow into the detector of the component of interest and correlating the detector output with the interruptions in the flow of the component of interest.

Accordingly to one aspect of the present invention a method of selectively distinguishing a component of interest from the remaining components in a fluid sample comprises periodically interrupting the flow of the component of interest to a detector and utilising the resulting difference output from the detector to indicate the presence and amount of the component of interest.

Conveniently the periodic switching can be effected by means of an oscillator and the output of the detector can be correlated to the oscillator. The interruption of the component of interest can be by destruction or conversion into products which do not elicite a response in the detector. The switching can occur at regular rapid intervals and can take place within a time range from 0.01 to 10 seconds. However a convenient switching frequency is anticipated to be in the range 0.1 to 3 seconds.

According to another aspect of the present invention an apparatus for selectively distinguishing a component of interest from the remaining components in a fluid sample comprises a detector sensitive to the presence of the component of interest and a switching valve in communication with the detector whereby fluid flows through the valve into the detector, and means for periodically switching the valve between a first and a second condition such that in the first condition the flow of the component of interest to the detector is interrupted without affecting the flow of the remaining components in the fluid sample, and, in the second condition all components in the fluid sample flow unimpeded into the detector.

The invention will now be described, by way of example only, with reference to the accompanying drawings in which:

FIG. 1 shows diagrammatically a known detector system for detecting the presence of a component in a gas flow;

FIG. 2 shows a detector system corresponding to FIG. 1 but modified in a manner according to the present invention;

FIGS. 3, 4 and 5 show alternative embodiments of switching devices, and

FIGS. 6, 7, 8 and 9 illustrate an arrangement for processing an output signal from the detector system.

In FIG. 1 an atmosphere to be sampled is drawn through a probe or nozzle 1 by means of a pump connected to a conduit 2. The incoming atmosphere impinges against a membrane separator 3, such as a silastomer membrane, and the components which pass through the membrane are carried by an inert carrier gas stream, for example argon, along a conduit 4 and into a detector 5, for example conventional electron capture detector.

An electron capture detector is an ionisation cell having a pair of spaced apart electrodes and a source of ionising radiation, such as tritium or $Ni_{63}$, therein. A carrier gas such as Argon flowing through the detector is ionised by emission from the source. By applying a voltage across the electrodes, and conveniently the voltage can be pulsed, electrons formed by the ionising radiation are collected at the anode to produce a detector standing current. If the carrier flow contains a material which is an electron absorber at least some of the electrons will be captured by the material resulting in a detectable change in the standing current.

The membrane 3 can be permeable to more than one component in the atmosphere. For example it is possible that both organic nitro vapours and halogenated hydrocarbons pass through the membrane and produce a response in the detector. An electron capture detector will produce a large output signal in the presence of an halogenated hydrocarbon or hydrocarbons, such as could be produced by the presence of pesticides in the sampled atmosphere. Consequently, if the detector was required to detect the presence of organic nitro-compounds in the sampled atmosphere it is possible that any resulting signal would be masked and remain undetected due to the presence of the other components which can pass through the membrane. In addition, there can be confusion and misunderstanding resulting from signals which are impossible to identify. The signals from the detector 5 can be amplified by an amplifier 6 and displayed on a meter or other form of recorder 7.

In FIG. 2, which shows one embodiment of the present invention, corresponding component parts are identified by the same reference numerals appearing in FIG. 1. In FIG. 2, a switching device 8 is located in the gas stream immediately in front of the detector 5, that is upstream of the detector. The switching device 8 can take a number of different forms and examples of switching devices are given hereinafter. The switching device 8 is switched on and off periodically, for example, by an oscillator 9 and the output from the detector 5 is correlated with the oscillator switching for example by means of a synchronous bridge 10. The detector 5 is provided with a polarising supply. Although the gas sample is shown as passing through a membrane it will be appreciated that this is not necessary and that the membrane does not form a part of the invention.

The arrangement of FIG. 2 is such that a vapour of interest in the gas stream to the detector is destroyed, or its flow otherwise interrupted, when the switching device 8 is switched on by the oscillator 9. The remaining components in the gas stream are not affected by the operation of the device 8. As a result, the periodic destruction or interruption of the component of interest in the flow to the detector causes an oscillation of the detector output and this oscillation of output will be superimposed on the outputs due to the remaining components which are unaffected by the switching of the device 8. As a result the output from the detector arising due to the presence in the gas stream of the remaining components can be substantially reduced when the detector output is correlated with the oscillator 9 by the synchronous bridge 10. The signals from the detector will be indicative of the presence of the vapour of interest and the magnitude of the signals will thus indicate the concentration of the vapour of interest.

The vapours of organic nitro explosives, such as nitro glycerine, ethylene glycol dinitrate, tri-nitro toluene and dinitro toluene produce a response in an electron capture detector. However on heating such organic nitro vapours to elevated temperatures which can be in excess of 200° C or a lower temperature in the presence of reactive substances such as solid catalysts, it is observed that they are broken down into components which do not produce a response in an electron capture detector. This property can be utilised as a basis for one form of switching device.

Again, for the sake of example, assume that the nitro explosives to be detected are present in an atmosphere which also contains halogenated hydrocarbons and oxygen, both of which can produce a response in an electron capture detector. Most halogenated hydrocarbons do not break down at the elevated temperatures mentioned above. Consequently it is possible to destroy the nitro-compounds and not the halogenated hydrocarbons in the gas flow to the electron capture detector by thermal degradation at a controlled temperature. Thus the switching device can comprise means for rapidly increasing and decreasing the temperature of the gas stream between a lower temperature at which all components pass through the device 8 into the detector and a higher temperature at which the nitro-compounds are broken down into components which do not elicite a response in the detector while the remaining halogenated hydrocarbons and the like responsive components pass unaffected into the detector. The periodic switching between the lower and higher temperatures can be effected at rapid intervals, for example at intervals of 1 second or less. This can be achieved in a number of ways, examples of which are as follows.

As shown in FIG. 3 switching device 8 can comprise a thin wall metallic tube 11 with the gas stream flowing in the indicated direction through the tube to the detector. The tube can be heated by direct ohmic heating. By passing an electric current by means of leads 12 through the wall of the tube the temperature can be increased rapidly to say 250° C or higher and the temperature can be regulated by control of the heating current. When the current is switched off the tube is cooled rapidly to the desired lower temperature. In practice this lower temperature will approach the maximum temperature at which the nitro compounds remain in their unbroken state so as to keep the temperature difference between the lower and higher limits as small as possible. Cooling of the tube can be by convection or by conduction through a heat sink 13 such as an oil bath, in intimate contact with the tube. The temperature of the heat sink can be controlled by means of an immersion heater 14.

Alternatively, the tube can be formed from a material, such as glass, which is either non-conducting or a poor conductor of electricity. Heating can be by means of a filament, for example a platinum wire, extending inside the length of the tube. The temperature can be controlled by monitoring the electrical resistance of the filament.

Another form of switching device 8 utilises a ferromagnetic wire coil maintained inside a glass or ceramic tube along which the sample flows to the detector. The tube itself is suspended in the coil of a radio-frequency oscillator. The wire coil can absorb energy rapidly from the radio-frequency field until the temperature of the coil reaches the Curie point. At this point the magnetic permeability of the coil falls suddenly and the absorbed energy falls rapidly so that the temperature of the coil is controlled at the Curie point. On switching off the oscillator the temperature falls rapidly. Conveniently use is made of a ferro-magnetic wire coil with a Curie point in the temperature range 250° to 400° C.

Another form of switching valve involves irradiating a heated quartz tube with ultra-violet radiation.

The nitroxy group : (O—$NO_2$) in nitro explosives gives an absorption band at about 270nm in the ultra violet region. The rate of decomposition of nitro compounds is slow at about 125° C but according to published papers the rate thereafter doubles with every 50° C temperature rise. Thus the sample to the detector is passed through a quartz tube maintained at an elevated temperature. Upon irradiation of the tube with ultra violet the nitro vapours are broken down into components which do not give rise to an output in the detector. The ultra violet radiation is pulsed periodically by means of the oscillator. A similar effect can be achieved using a pulsed laser of high intensity.

Yet another form of switching device can utilise the strong electron capture properties of certain compounds. Upon capturing an electron, an electro-negative species forms a negative ion which either dissociates or discharges on positive ions or at an electrode resulting in the destruction of the electro-negative species and the production of non-electron capturing products.

As an alternative to the above, a switching device can comprise an ionisation chamber in which thermal electrons are produced in pulses by irradiation of a photosensitive layer. Thus thermal electrons can be produced by irradiating a thin layer of material capable of emitting electrons by photo-emission with ultra-violet light. A suitable material can be gold, silver or palladium, or an alloy of such materials. Such a photo-sensitive layer can be deposited by evaporation on the interior of the ionisation chamber. Ultra-violet light can be periodically directed against the deposited photo-sensitive layer to produce a high electron density within the chamber, the pulsing of the light source being under the control of the oscillator. The electrons produced can have a half life of approximately 1ms and can be removed by collision with the walls of the chamber or are swept out of the chamber with the gas flow. It is possible to control the electron density within the chamber such that it varies between a low value, for example zero, and a value sufficient to ensure substantially 100% probability of capture by strong absorbers in the gas flow.

Instead of utilising a single flow path it is possible to switch the gas flow to the detector between two separate paths. One of the paths can be maintained at a high temperature and the other at a lower temperature.

Thus with reference to FIG. 4, a switching device 8 comprises two separate flow paths having a common inlet 15 for the incoming gas flow and a common outlet 16 leading to a detector. Flow path 17 is maintained at a temperature at which constituents of interest in the gas flow, such as nitro-compounds, are broken down into components which do not elicite a response in the detector. As before the temperature of flow path 17 can be maintained by direct ohmic heating of the wall of the flow path through leads 18. Flow path 19 is maintained at a temperature below the breakdown temperature of the constituent of interest. Whilst the flow path 19 can be at ambient temperature it is preferable to contain both the flow paths 17 and 19 together with the inlet 15 and outlet 16 within a heated enclosure in order to minimise the possibility of constituents in the gas flow sticking to the walls of the flow paths and conduits. The heated enclosure, which can be at a temperature in the region of 150° C, is indicated by the dotted outline 20.

A switching means 21, such as an electro-magnetically operable valve, is included at the junction of the inlet 15 and the two flow paths 17 and 19. A valve closure member, for example a ball 22, is movable between the ends of the valve housing whereby to alternately open and close the inlets to the respective flow paths 17 and 19. The movement of the closure member is controlled by the oscillator.

FIG. 5 illustrates diagrammatically an alternative arrangement in which a switching means 23 is located outside the heated enclosure. The hot flow path is indicated by reference numeral 24 and the cooler path by reference numeral 25. Numerals 26 and 27 respectively indicate flow paths to the switching means 23 which is also connected to atmosphere, conveniently at the exhaust side of the detector.

Purely as examples, the hot flow path 24 and the cooler flow path 25 can each be formed from a tube having a wall thickness of 0.15mm, an outside diameter of 1.5mm and a length of 200mm. Conveniently the tubes will be coiled for compactness. The flow paths 26 and 27 can each be formed from tubes of length 50mm and bore 0.25mm. The remaining portions of the flow paths leading to the detector are denoted diagrammatically by the reference numerals 28 and 29. These are likewise equal and each can be formed from tubes of length 75mm and bore 0.25mm.

The arrangement ensures a substantially constant flow through the detector and equal flows in the two separate flow paths. In the illustrated position of the switching means 23 sample flow through the cooler tube 25 proceeds to the detector while the flow through the hot tube exhausts to atmosphere. In the other position of the switching means the flow through the hot tube proceeds to the detector with the cooler flow being exhausted to atmosphere.

Another form of switching valve can employ chemical reactions for the periodic destruction of the component of interest in the gas sample. Thus the flow to the detector can be periodically switched to pass through a reaction chamber containing a reagent capable of converting the component of interest into a product which will not produce an output signal from the detector. The remaining components in the gas flow will remain unaffected by passage through the reaction chamber. This periodic switching of the gas flow between a direct path to the detector and a path containing the reaction chamber can be controlled by an oscillator or the like in the manner outlined above.

Still yet another form of switching valve can rely on the oxidation of the component of interest. The gas flow to the detector can be switched periodically between a cold path and a heated path containing a catalyst capable of oxidising the component of interest, but not the remaining components in the gas flow. The detector chosen will be sensitive to the component of interest but will not respond to the oxidation product or products. Such a detector is the flame ionisation detector which is sensitive to all hydrocarbons but not the products of complete oxidation, which are carbon dioxide and water vapour.

It is possible to utilise the invention to distinguish the presence in a gas flow of a constituent which normally does not produce a response in the detector. Thus such a constituent can be converted into a product which will give rise to a response in the detector by means of a switching device.

As an example only it is possible to convert olefins which are non-electron capturing into electron capturing products. This can be achieved by the selective chlorination of the olefins. The chlorine can be produced electrolytically with the electrolytic process being under the control of the oscillator or the like as in the previous examples. Excess chlorine can be removed by passing through a suitable extractor, such as sodium phosphite, before the reaction product enters the detector.

It will be apparent from the above that the switching device can take a variety of different forms and that the examples given are not exhaustive of all possible forms of the device. The switching devices can be employed with a variety of detectors, such as an electron capture detector, an argon ionisation detector, a thermal conductivity detector and a flame ionisation detector, to enable the detector to selectively distinguish the presence of a component of interest in a gas flow. By appropriate choice of switching device and detector it is possible to detect other constituents in a gas sample in addition to the vapours or organic nitro explosives. Thus, for example, the invention can be used to detect the vapours emitted by drugs.

FIG. 6 shows an arrangement for processing signals from the detector. In FIG. 6 a switching device, which can take the form as hitherto described, is indicated by the reference numeral 30 and a detector by the reference numeral 31.

The detector output is fed to a band pass filter amplifier 32 which allows only signals of frequency close to the switching frequency to be passed through. The output from the band pass filter amplifier 32 enters a synchronous bridge or lock-in amplifier 33 having two signal paths 34 and 35 respectively. Path 34 allows the signals to pass unchanged while path 35 includes a signal inverter 36. A switch 37 is operated synchronously with the switching device 30 by means of a control oscillator 38. This switch 37 gates the signal and the inverted signal alternately into an RC filter 39 which provides a suitable time constant. The output an X with the signals of interest and the reference signal from the oscillator in synchronism will be a D.C. voltage signal proportional to the amplitude of the signal of interest.

FIG. 7 is a graphical representation of a typical detector response plotted against time. In the presence in the gas sample of a detectable trace material which is not affected by the switching device, for example a halogenated hydrocarbon, the detector response will be a substantially smooth curve as represented at the left hand side of the diagram. The response arising from the presence of a switched constituent, for example a nitro-compound which is alternately switched between a hot and cold path leading to the detector, will be as indicated at the right hand side of the diagram. If both forms of detectable materials are present concurrently in the gas sample then the two responses will be superimposed one upon the other.

As mentioned, the detector response can be fed to the band pass filter amplifier 32 which functions to pass only signals having a frequency close to the switching frequency of the switching device 30. FIG. 8 illustrates a typical signal output from the filter amplifier 32.

FIG. 9 illustrates a typical output signal received at X in FIG. 6 due to the alternate switching of the output from the filter amplifier 32 between the paths 34 and 35. For normal random noise the sum of the inverted and non-inverted signal will be zero. Signal drifts and responses which are not in synchronisation with the switching frequency are eliminated while synchronous signals are converted in the RC network to provide a steady D.C. signal output.

We claim:

1. A method for selectively distinguishing a constituent of interest from the remaining constituents in a gas sample, comprising:
   continuously flowing sample gas through a switching device into a detector;
   heating the switching device:
   alternately raising and lowering the temperature of the gas flow furnished by the switching device to said detector above and below a temperature at which the flow to the detector of the consitutent of interest is interrupted without affecting the flow of the remaining consititutents in the sample gas, such alternating raising and lowering of the temperature including periodically switching a condition of the switching device;
   monitoring output signals from the detector and correlating such detector output signals with the switching of said switching device and from such correlation indicating the presence and concentration of the constituent of interest in the gas flow.

2. The method of claim 1 in which said temperature at which said flow of said constituent of interest is interrupted is the temperature at which the constituent of interest breaks down into components which are capable of detection in the detector.

3. The method of claim 1 including routing of all gas through a single flow path through said switching device and providing in such single flow path a thin-wall metal tube capable of rapid heating and cooling, said step of switching the switching device including turning on and off a supply of electrical heating current to such tube.

4. The method of claim 1 in which the sample gas is routed through said switching device in two separate flow paths, the step of alternately raising and lowering the temperature of the gas flow including heating one of the two flow paths in the switching device to said temperature at which the flow of the constituent of interest is interrupted and using the periodic switching of said switching device to supply gas to the detector alternatively and repetitively from the heated and non-heated flow paths through the switching device.

5. An apparatus for selectively distinguishing a detectable constituent of interest from the remaining detectable constituents in a gas flow, comprising:
   a gas flow path;
   a detector in said gas flow path and which is responsive to at least said constituent of interest in said gas flow for emitting a corresponding signal;
   a switching means intervening in said gas flow path upstream of said detector and periodically switchable for alternately raising and lowering the temperature of the gas flow to the detector above and below the temperature at which the flow of the constituent of interest is interrupted without affecting the flow of the remaining constituents;
   means for heating said switching means;
   means for periodically switching said switching means;
   means for correlating fluctuations of said detector signal with the periodic switching of said switching device to indicate the presence and concentration of said constituent of interest in said gas flow.

6. The apparatus of claim 5 in which said flow interruption temperature is the temperature at which the constituent of interest breaks down into components incapable of detection by said detector.

7. The apparatus of claim 6 in which said switching means has a single flow path therethrough and includes a thin-walled metal tube comprising at least a length segment of such single flow path through said switching means, said periodic switching including means passing an electric current through the wall of said thin-walled tube for heating said tube and an alternating electrical supply connected thereto, said switching means further including a heat sink in heat conducting engagement with said thin-walled metal tube for rapidly cooling same upon shut-off of electrical current flow through said tube.

8. The apparatus of claim 5 in which said switching means comprises two separate and parallel flow paths having a common inlet to receive sample gas flow and a common outlet communicating with the input of the detector, said means for heating said switching device including means continuously heating one of said two separate flow paths, said switching means comprising valve means connected to said two separate flow paths and causing the flow of gas to the detector to be first from one said separate flow path and then from the other in a repetitive alternating manner.

9. The apparatus of claim 8 in which said means for heating said switching means includes a first means for so controlling the heat of said separate flow paths that the cooler thereof is at a temperature close below the breakdown temperature of the constituent of interest, said means for heating the switching means further including means specifically heating the hotter of said two separate flow paths to a temperature immediately above said breakdown temperature.

10. The apparatus of claim 9 in which said valve means includes a valve interposed in a flow path at the input ends of said two separate flow paths and repetitively actuable to alternately close the input of first one then the other flow path.

11. The apparatus of claim 9 including flow resistance means at the output ends of said separate two flow paths through said switching means, said valve means including a valve coupled to said two flow paths ahead of said flow resistance for shunting the flow first from one path and then from the other in an alternating fashion such that such paths empty in complementary alternating fashion into said detector.

12. The apparatus of claim 5 in which said heating means comprises a heated enclosure in which said switching means and the gas flow path are disposed.

13. The apparatus of claim 5 in which said correlating means includes band pass means for passing only those detector output signals of frequency close to the switching frequency, said means for periodically switching said switching means including an alternating frequency signal source of controlled frequency, said means for correlating further including gating means having alternatively selectable first and second inputs respectively connected directly and through inverting means to the output of said band pass means, said gating means further including a control input connected to said alternating frequency source for alternately applying at such frequency the signals on the first and second gating means inputs to a common output of said gating means, and filter means connected to said common output and having a preselected time constant for providing an output of d.c. magnitude corresponding to the component of interest.

14. An apparatus for selectably distinguishing a detectable constituent of interest from the remaining detectable constituents in a gas flow, comprising:
   a gas flow path;
   a detector in said gas flow path and which is responsive to at least said constituent of interest in said gas flow path for emitting a corresponding signal;
   a switching device in said gas flow path upstream of said detector, said switching device being capable of providing a substantially uninterrupted flow of gas to said detector, said switching device including separate, parallel first and second paths therethrough, said first path providing a direct unobstructed passage to said detector and said second path containing a chemical reagent capable of interrupting the flow of the constituent of interest in said gas flow while leaving unaffected remaining components of such gas flow;
   flow switching means alternatively connectible to said first and second paths of said switching device for causing the detector to receive flow alternatively and repetitively from said first and second paths respectively;
   means responsive to fluctuations in the output signal of said detector and the periodic switching of said switching means for indicating the presence and concentration of said constituent of interest in said gas flow.

15. The apparatus of claim 14 including an oscillator for driving said switching means, said means responsive to fluctuations including a synchronous converter coupled to the detector output and 16. The apparatus of claim 14 in which said switching device includes means for periodically converting a constituent of interest which normally fails to produce a response in the detector into a product capable of producing a response in the detector.

* * * * *

UNITED STATES PATENT OFFICE
CERTIFICATE OF CORRECTION

Patent No. 4,019,863                    Dated April 26, 1977

Inventor(s) Anthony Jenkins and James Ephraim Lovelock

It is certified that error appears in the above-identified patent and that said Letters Patent are hereby corrected as shown below:

Column 10, line 32; after "detector output and"

insert ---said oscillator.---.

Signed and Sealed this twenty-sixth Day of July 1977

[SEAL]

Attest:

RUTH C. MASON  
*Attesting Officer*

C. MARSHALL DANN  
*Commissioner of Patents and Trademarks*